United States Patent [19]

Blazey

[11] Patent Number: Plant 5,448

[45] Date of Patent: Apr. 30, 1985

[54] ROSE PLANT—BLABEE

[75] Inventor: Daniel Blazey, Toledo, Ohio

[73] Assignee: Nor'East Miniature Roses, Inc., Rowley, Mass.

[21] Appl. No.: 535,738

[22] Filed: Sep. 26, 1983

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose variety of Rhodonite red and green-white.

1 Drawing Figure

The present invention relates to a new and distinct variety of rose plant of the miniature rose class, which was originated by my crossing as seed parent the rose known as "Little Darling" (U.S. Plant Pat. No. 1,581) and the rose known as "Toy Clown" (U.S. Plant Pat. No. 2,909) as pollen parent. The varietal denomination of the new variety is "Blabee".

Among the novel characteristics possessed by this new variety which distinguish it from its parents and all other varieties of which I am aware are bicolored flowers of Rhodonite Red and green-white coloring borne on an upright growing plant one to a stem and in clusters of as many as eight blooms. The flower coloring varies from a red coloring washing onto a green-white base in some petals to other petals with little or no coloring admixture or washing. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminolgy in accordance with The Royal Horticultural Society Colour Chart (R.H.S.C.C.). The terminology used in color description herein refers to plate numbers in the aforementioned color chart, e.g., "157B" is plate 157B of The Royal Horticultural Society Colour Chart.

Parentage: Seedling.

*Seed parent.*—"Little Darling".

*Pollen parent.*—"Toy Clown".

Class: Miniature.

The following observations are made of specimens grown outdoors in Essex County, Mass. during the month of July.

FLOWER

Blooming habit: Recurrent.

Bud:

(1) *Size.*—Small.

(2) *Form.*—Short pointed.

(3) *Color.*—When sepals first divide — green-white 157B edged with 50C. When petals begin to unfurl — Petal top surface Rhodonite red 51A to 51C; Petal undersurface 157C to 157B.

(4) *Sepals.*—Slightly foliated, longer than bud.

(5) *Peduncle.*—Length — $\frac{3}{4}$ to 1 inch. Aspect — straight. Strength — erect. Color — near 144A.

Bloom:

(1) *Size.*—Average size when fully expanded — about $1\frac{1}{2}$ inches.

(2) *Borne.*—Singly and sprays of 4 to 8 blooms.

(3) *Form.*—High centered at first, becoming flat.

(4) *Petalage.* —Number of petals under normal conditions — about 30 to 40.

(5) *Color.*—In bud form after the sepals first divide the color initially seen is green-white 157B edged with 50C. When the petals begin to unfurl, the petal top surface is Rhodonite red 51A to 51C. The petal undersurface remains green-white in coloring near 157C to 157B. As sepals fall, green-white 157C petal undersurface is seen. Slight red edging 50C is also visible but mainly at the petal edge until petals unfurl further. As flower opens, Rhodonite red coloring of petal top surface becomes visible. As interesting characteristic is that the red coloring (varying from Rhodonite red 51A, 51B, Crimson 52A and Carmine 52B) appears as a red coloring washing on 157C in some petals and in other petals the red coloring 51A and 51B makes up the predominant color with little or no washing or color admixture. In still another variation some flowers display petal top surfaces which are primarily 157C with lesser red coloring and washing. The result is that on the plant there is an array of varicolored flowers of basically similar coloring but which may differ from each other.

Petals:

(1) *Texture.*—Average.

(2) *Appearance.*—Inside satiny, outside velvety.

(3) *Form.*—Rounded oval with short pointed apex.

(4) *Arrangement.*—Regularly arranged.

(5) Petaloids in center.—Few.

(6) *persistence.*—Drop off cleanly.

(7) *Fragrance.*—None.

(8) *Lasting quality.*—Average on plant and as cut flower.

REPRODUCTIVE ORGANS

Stamens, filaments and anthers:

(1) *Arrangement.*—Regularly arranged around styles.

(2) *Color.*—Near 163B.

Pollen:

*Color.*—Near 163A.

Styles: Even, medium length.

Stigmas:

*Color.*—Near 48B.

Hips; None observed.

PLANT

Form: Upright, compact

Growth: Vigorous, uniform branching, symmetrical.

*Height attained.*—About 12 to 16 inches.

Foliage: Compound 5 to 7 leaflets.

(1) *Size.*—Medium.

(2) *Quantity.*—Abundant.

(3) *Color.*—New foliage: Upper side — near to 137A. Under side — near to 148B. Old foliage: Upper side — near 137A. Under side — near 146B.

(4) *Shape.*—Oval pointed.

(5) *Texture.*—Upper side is medium glossy and under side is matte.

(6) *Edge.*—Serrated.

(7) *Serration.*—Light, shallow.

(8) *Leaf stem.*—Color — near to 146A. Under side — near 146B.

(9) *Stipules.*—Medium, smooth.

(10) *Resistance to disease.*—Blackspot — average. Mildew — average.

Wood:

(1) *New wood.*—Color — near 146B. Bark — Smooth.

(2) *Old wood.*—Color — near 137B. Bark — smooth.

Thorns:

(1) *Thorns.*—Quantity (main stalk) — few , short. On laterals from stalk — few. Form — straight, thin, pointed, angled slightly downward. Length — short. Color — near 181C. Position — irregular.

(2) *Prickles.*—None.

Winter hardiness: Requires ordinary protection in extreme climates.

I claim:

1. A new and distinct variety of rose plant of the miniature rose class, substantially as shown and described, characterized particularly by Rhodonite red and green-white bicolored flowers of good form borne one to a stem and clusters of four to eight blooms on a vigorous, attractive plant.

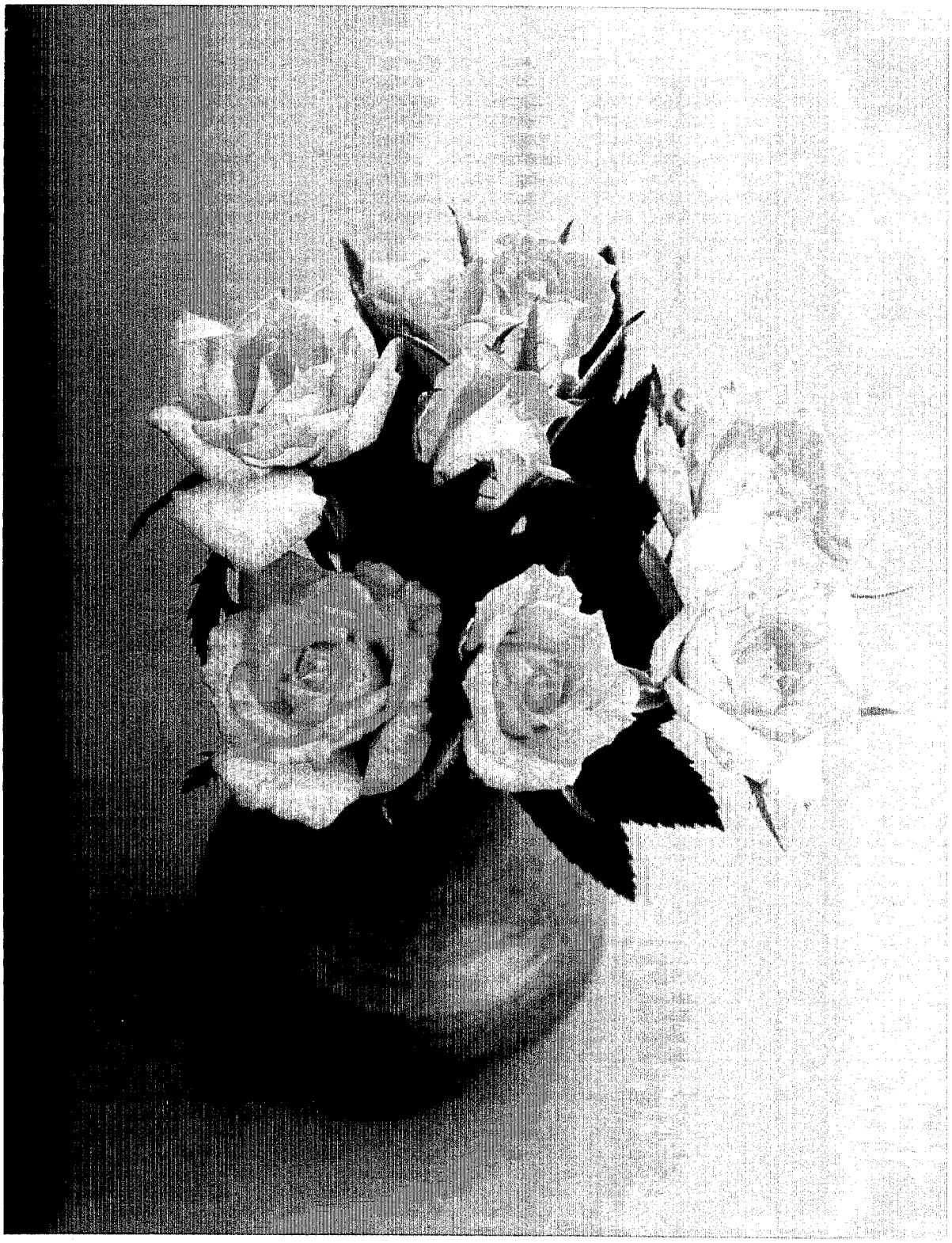

* * * * *